(12) United States Patent
Yoshimura

(10) Patent No.: US 11,241,144 B2
(45) Date of Patent: Feb. 8, 2022

(54) MEDICAL SYSTEM AND OPERATION METHOD OF MEDICAL SYSTEM

(71) Applicant: OLYMPUS CORPORATION, Tokyo (JP)

(72) Inventor: Katsuhiko Yoshimura, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 82 days.

(21) Appl. No.: 16/881,286

(22) Filed: May 22, 2020

(65) Prior Publication Data
US 2020/0281449 A1    Sep. 10, 2020

Related U.S. Application Data

(63) Continuation of application No. PCT/JP2017/042573, filed on Nov. 28, 2017.

(51) Int. Cl.
*A61B 1/00* (2006.01)
*A61B 1/04* (2006.01)
(Continued)

(52) U.S. Cl.
CPC ........ *A61B 1/00149* (2013.01); *A61B 1/0005* (2013.01); *A61B 1/00006* (2013.01);
(Continued)

(58) Field of Classification Search
CPC ............ A61B 1/00149; A61B 1/00006; A61B 1/00009; A61B 1/00039; A61B 1/0005; A61B 1/042; A61B 1/3132
See application file for complete search history.

(56) References Cited

U.S. PATENT DOCUMENTS

| 5,836,869 A | 11/1998 | Kudo et al. |
| 8,725,399 B2 * | 5/2014 | Nonaka ................. G06T 11/206 |
| | | 701/446 |

(Continued)

FOREIGN PATENT DOCUMENTS

| JP | H08-164148 A | 6/1996 |
| JP | 4027876 B2 | 12/2007 |

(Continued)

OTHER PUBLICATIONS

International Search Report dated Feb. 27, 2018 issued in PCT/JP2017/042573.

(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A medical system has a treatment device having a reference-position designation portion, an endoscope acquiring a plurality of captured images, a storage device, a controller generating a plurality of display images corresponding to the captured images, and a display. The controller determines an arbitrary position in the display image as a reference position, detects a region in the display image where the treatment device is displayed as an excluded region and selects a reference image from a region in the display image excluding the excluded region, records the reference image in the storage device, calculates a relative position from the reference position to the reference image, detects the reference image from the plurality of display images after the reference image is generated, recognizes the reference position in the display image, and controls an operation of the endoscope to make the reference position to be coincided with a target position.

13 Claims, 11 Drawing Sheets

(51) Int. Cl.
  *A61B 1/045* (2006.01)
  *A61B 1/313* (2006.01)
(52) U.S. Cl.
  CPC ...... *A61B 1/00009* (2013.01); *A61B 1/00039* (2013.01); *A61B 1/042* (2013.01); *A61B 1/045* (2013.01); *A61B 1/3132* (2013.01)

(56) References Cited

U.S. PATENT DOCUMENTS

| | | | |
|---|---|---|---|
| 9,757,206 B2* | 9/2017 | Frimer | A61B 1/3132 |
| 10,321,803 B2* | 6/2019 | Gilboa | A61B 5/415 |
| 10,555,775 B2* | 2/2020 | Hoffman | A61B 1/04 |
| 2020/0100649 A1* | 4/2020 | Inoue | A61B 1/00133 |

FOREIGN PATENT DOCUMENTS

| | | |
|---|---|---|
| JP | 2012-239644 A | 12/2012 |
| JP | 2015-154873 A | 8/2015 |
| JP | 2016-504067 A | 2/2016 |
| WO | WO 2014/115901 A1 | 7/2014 |

OTHER PUBLICATIONS

Japanese Notice of Allowance dated Feb. 24, 2021 received in 2019-556430.

* cited by examiner

CURRENT TIME t1 TIME BEFORE t2 TIME BEFORE

MEDICAL SYSTEM AND OPERATION METHOD OF MEDICAL SYSTEM

This application is a continuation application based on a PCT International Application No. PCT/JP2017/042573, filed on Nov. 28, 2017. The contents of the PCT International Application are incorporated herein by reference.

BACKGROUND

Field of the Invention

The present invention relates to a medical system configured to perform treatment through a hole formed on the abdominal wall and the like and an operation method of the medical system.

Description of Related Art

Conventionally, in the laparoscopic surgery, treatment method of inserting a treatment device, an endoscope and the like into separate holes (openings) opened on the abdominal wall is known. The endoscope and the treatment device inserted into the body (abdominal cavity) is independently operated with each other. In order to provide the most suitable field of view of the endoscope to the surgeon, for example, a field of view including a region-of-interest such as the treatment target site and the like, it is necessary for a scopist operating the endoscope to move the endoscope to the most suitable position for the treatment.

The surgeon and the scopist have to efficiently communicate with each other so as to provide the most suitable field of view of the endoscope to the surgeon. It is necessary for the surgeon to interrupt the treatment and wait for the adjustment of the field of view of the endoscope being finished if the scopist cannot move the endoscope such that the region-of-interest of the surgeon is not included in the image captured by the endoscope.

In Japanese Patent No. 4027876, an intracavity observation system configured to provide a color marker on a distal end of the treatment device is disclosed, wherein the intracavity observation system is configured to determine a position of the color marker from the image captured by the endoscope and operate the endoscope so as to make the determined position of the color marker is at the center of the image. The scopist does not directly operate the endoscope and the endoscope is operated to cause the distal end of the treatment device to be positioned at the center of the image.

In the intracavity observation system disclosed in Japanese Patent No. 4027876, the endoscope is operated such that the distal end of the treatment device so as to always follow the distal end of the treatment device. Accordingly, it is not always that the image captured by the endoscope is an image including the region-of-interest of the surgeon. For example, in a situation when the position of the distal end of the treatment device is moved to a region where is not the region-of-interest of the surgeon, the image captured by the endoscope is an image captured following the distal end of the treatment device which the region-of-interest of the surgeon is not included therein.

SUMMARY

According to a first aspect of the present invention, a medical system has a treatment device having a reference position designation portion; an endoscope which is electrically driven and configured to acquire a plurality of captured images; a storage device configured to record the plurality of captured images; a controller configured to generate a plurality of display images corresponding to the plurality of captured images acquired by the endoscope; and a display configured to display the plurality of display images, wherein the controller is configured to: determine an arbitrary position designated by the reference position designation portion in one of the plurality of display images as a reference position, detect a region in the display image where the treatment device is displayed as an excluded region and select a reference image with a predetermined size from a region in the display image excluding the excluded region, record the reference image in the storage device, calculate a relative position from the reference position to the reference image, detect the reference image from the plurality of display images after the reference image is generated, and recognize the reference position in the display image according to the position of the reference image and the relative position, and control an operation of the endoscope so as to make the reference position to be coincided with a target position on the display image after the reference image is generated.

According to a second aspect of the present invention, in the medical system according to the first aspect, the controller may be configured to select an image of the adjacent region as the reference image and detect an adjacent region which is adjacent to the reference position.

According to a third aspect of the present invention, in the medical system according to the second aspect, the controller may be configured to select an image of the adjacent region as the reference image, where a distance between a center of the selected adjacent region and the excluded region is the largest.

According to a fourth aspect of the present invention, in the medical system according to the second aspect, the controller may be configured to select an image of a non-adjacent region from a plurality of non-adjacent regions being not adjacent to the reference position as the reference image, where a distance between a center of the selected non-adjacent region and the reference position is the smallest, when none of adjacent region being adjacent to the reference position can be secured.

According to a fifth aspect of the present invention, in the medical system according to the first aspect, the controller may be configured to select and update the reference image when the controller determines that the reference position and the target position coincide with each other.

According to a sixth aspect of the present invention, in the medical system according to the first aspect, the controller may be configured to store the reference image selected from the adjacent region or the non-adjacent region in the storage device as a first reference image, store the reference image selected from a region in the non-adjacent region where the first reference image is not included in the storage device as a second reference image, and determine the second reference image as the reference image when none of the first image is detected in the plurality of display images generated after the reference image is selected.

According to a seventh aspect of the present invention, in the medical system according to the first aspect, at the time of selecting the reference image from the display image after an activate instruction for activating the controller is input, the controller may be configured to select the reference image from the display image before the activate instruction.

According to an eighth aspect of the present invention, in the medical system according to the first aspect, the reference position designation portion may be a distal end of the treatment device.

According to a ninth aspect of the present invention, in the medical system according to the first aspect, the target position may be a center of the display image.

According to a tenth aspect of the present invention, an operation method of a medical system, wherein the medical system having a treatment device having a reference position designation portion, an endoscope which is electrically driven and configured to acquire a plurality of captured images, a storage device configured to record the plurality of captured images, a controller configured to generate a plurality of display images corresponding to the plurality of captured images acquired by the endoscope, and a display configured to display the plurality of display images, has a process of determining an arbitrary position designated by the reference position designation portion in one of the plurality of display images as a reference position; a process of detecting a region in the display image where the treatment device is displayed as an excluded region and selecting a reference image with a predetermined size from a region in the display image excluding the excluded region; a process of recording the reference image in the storage device; a process of calculating a relative position from the reference position to the reference image; a process of detecting the reference image from the plurality of display images after the reference image is generated and recognizing the reference position in the display image according to the position of the reference image and the relative position, and a process of controlling an operation of the endoscope so as to make the reference position to be coincided with a target position on the display image after the reference image is generated.

According to an eleventh aspect of the present invention, in the operation method of a medical system according to the tenth aspect, the process of determining the reference image may include a process of judging whether an adjacent region being adjacent to the reference position can be secured and determining the adjacent region.

According to a twelfth aspect of the present invention, in the operation method of a medical system according to the eleventh aspect, when it is determined that the adjacent region can be secured in the process of determining the reference image, a process of selecting an image of the adjacent region as the reference image may be included, wherein a distance between a center of the selected adjacent region and the excluded region is the largest.

According to a thirteenth aspect of the present invention, in the operation method of a medical system according to the tenth aspect, when it is determined that the none of adjacent region can be secured in the process of determining the reference image, a process of selecting an image of a non-adjacent region from a plurality of non-adjacent regions being not adjacent to the reference position as the reference image may be included, wherein a distance between a center of the selected non-adjacent region and the reference position is the smallest.

DETAILED DESCRIPTION OF EMBODIMENTS

First Embodiment

A first embodiment of the present invention will be described referring to FIG. 1 to FIG. 12. In order to make the images easy to view, dimensions of each configuration element is suitably adjusted.

Figure 1:
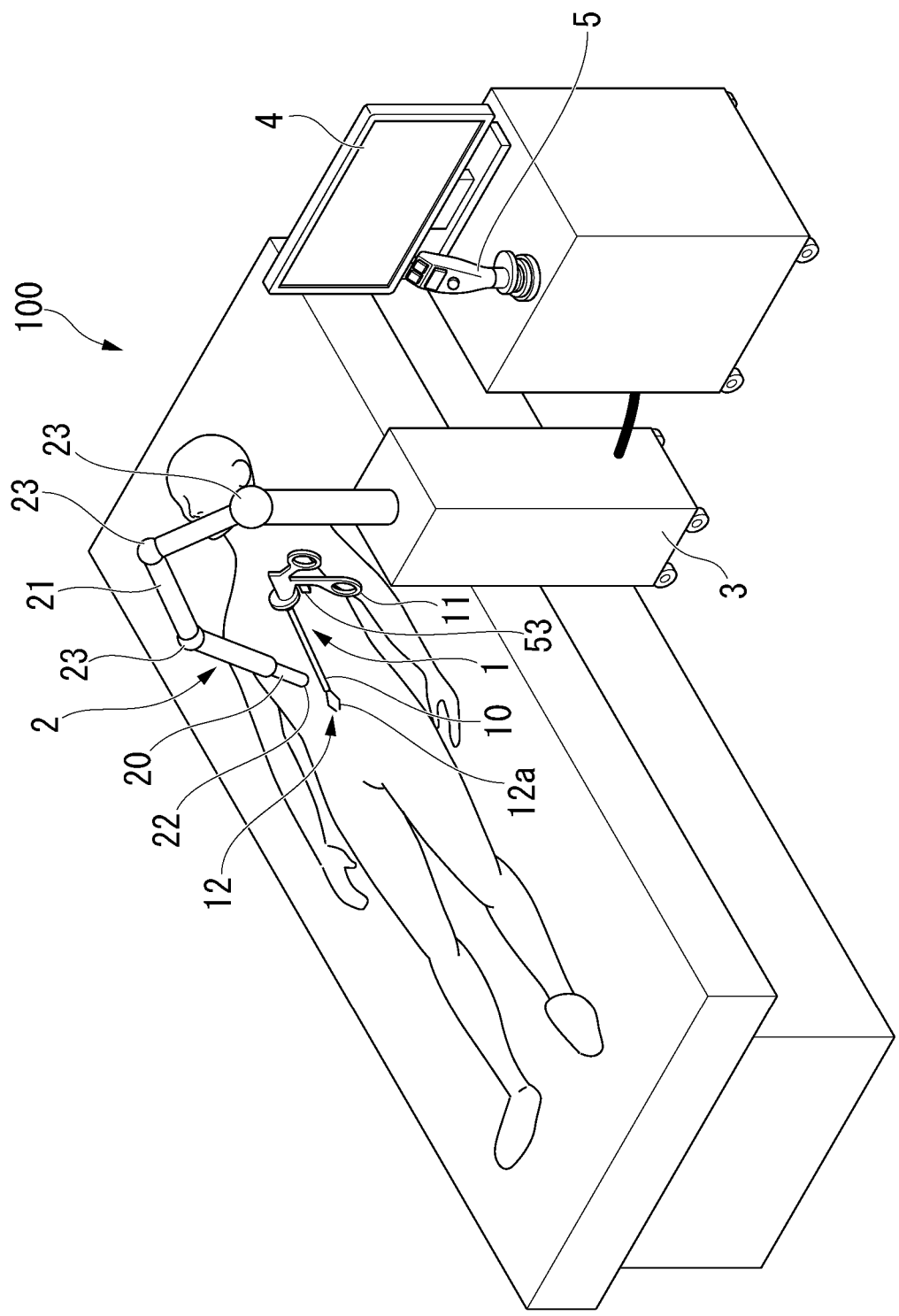
FIG. 1 is a view showing an overall configuration of a medical system according to a first embodiment of the present invention.

FIG. 1 is a view showing an overall configuration of a medical system 100 according to the present embodiment.

As shown in FIG. 1, the medical system 100 has a treatment device 1, an endoscope 2, a control apparatus (controller) 3, a display apparatus (display) 4, and an input device (input) 5. The medical system 100 is configured to assist the treatment of inserting the treatment device 1, the endoscope 2 and the like through separate holes (openings) opened on the abdominal wall during the laparoscopic surgery.

As shown in FIG. 1, the treatment device 1 has an insertion portion 10 configured to be insertable into the body (abdominal cavity) of the patient and an operation portion 11 disposed at a proximal end portion of the insertion portion 10. The surgeon inserts the insertion portion 10 through a trocar penetrating the abdominal area of the patient to introduce the insertion portion 10 into the body (abdominal cavity). Due to the variations of the treatment and the situation of the lesion area, the surgeon may introduce a plurality of treatment devices 1 into the body (abdominal cavity).

As shown in FIG. 1, the insertion portion 10 has a treatment portion (end effector) 12 on a distal end portion of the insertion portion 10, wherein the treatment portion 12 is configured to perform treatment to the lesion area of the patient. The treatment portion 12 according to the present embodiment has a grasp mechanism configured by a pair of grasping members 12a.

The operation portion 11 is a member configured to operate the pair of grasping member 12a. The operation portion 11 has a handle, wherein the pair of the grasping member 12a are opened/closed by relatively moving the handle with respect to other portions of the operation portion 11. The surgeon can operate the treatment portion 12 while holding the operation portion 11 by single hand.

Figure 2:
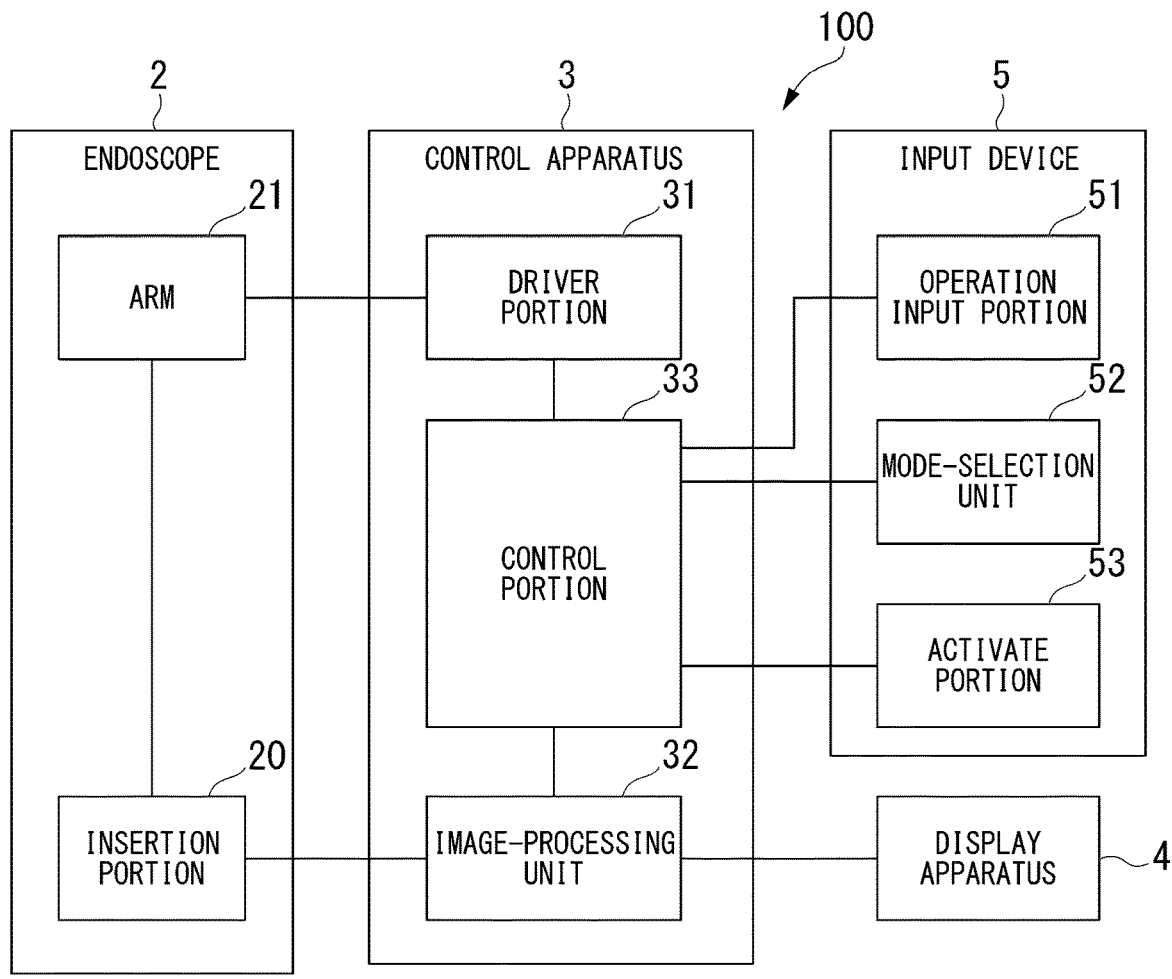
FIG. 2 is a view showing a hardware configuration of the medical system.

FIG. 2 is a view showing a hardware configuration of the medical system 100 excluding the treatment device 1.

As shown in FIG. 1 and FIG. 2, the endoscope 2 has an elongated insertion portion 20 configured to be insertable into the body (abdominal cavity) of the patient and an arm 21. The surgeon inserts the insertion portion 20 through the trocar penetrating the abdominal area of the patient to introduce the insertion portion 20 into the body (abdominal cavity).

The insertion portion 20 is configured to have an imaging portion 22 disposed at the distal end portion thereof, wherein the insertion portion 20 has lens and image sensor configured to capture the situation inside the body (abdominal cavity) of the patient. The insertion portion 20 introduced into the body (abdominal cavity) is disposed at a position where the imaging portion 22 can capture the image of the lesion area as the treatment target inside the body (abdominal cavity). The imaging portion 22 may have the optical zoom function or the electrical zoom function.

The insertion portion 20 may further have an active bending portion which can bend actively. The orientation of the lens and the image sensor of the imaging portion 22 can be changed by bending the active bending portion disposed at part of the insertion portion 20.

As shown in FIG. 1, the arm 21 is an electric-drive robot arm having at least one joint 23. A distal end of the arm 21 is connected to the proximal end portion of the insertion portion 20 of the endoscope, and the arm 21 is configured to be able to move the insertion portion 20.

The joint 23 is a portion to be bent around a rotation axis as a rotation center, wherein the joint 23 may be a configuration to be actively bendable due to a motor and the like, and the joint 23 may be a configuration to be passively bent by advancement and retraction of the wires and the like connected thereto. Inside the arm 21, control signal line configured to control the bending of the joint 23 and the wires are disposed thereto. Inside the arm 21, the control signal line configured to control the imaging portion 22 and the transmission signal line configured to transmit the captured image captured by the imaging portion 22 are disposed thereto.

As shown in FIG. 2, the control apparatus 3 has a driver portion 31, an image-processing unit 21, and a control portion 33. The control apparatus 3 is configured to control the arm 21 and the like according to the input from the input device 5. The control apparatus 3 is configured to generate a display image from the captured image which is captured by the imaging portion 22 of the endoscope 2 and transmit the display image to the display apparatus 4.

The driver portion 31 is configured to drive the joint 23 of the arm 21. In the situation when the joint 23 is configured to bend actively, the driver portion 31 is configured to generate the control signal for the motor and the like to operate the joint 23. In the situation when the joint 23 is configured to be bent passively, the driver portion 31 is configured to control the advancement and the retraction of the wires for operating the joint 23. In each situation shown above, the driver portion 31 is controlled by the control portion 33.

The image-processing unit 32 is connected by the transmission signal of the captured image which is captured by the imaging portion 22, and the image-processing unit 32 is configured to acquire the captured image via the transmission signal. The image-processing unit 32 is configured to generate the display image for display from the captured image. The image-processing unit 32 may be configured to perform image processing with respect to the captured image such as image format transformation, contrast adjustment and the like. The generated display image is transmitted at predetermined transmission timing to the display apparatus.

The image-processing unit 32 can generate the display image by replacing images such as figures or characters generated by the control portion 33 with the captured image or superimposing the images such as figures or characters generated by the control portion 33 on the captured image. For example, the image-processing unit 32 can superimpose the images of characters corresponding to the warnings and operation assistance for the surgeon on the captured image so as to generate the display image.

Also, the images such as the figures and the characters shown above may be generated by the image-processing unit 32 according to the instructions from the control portion 33 rather than the control portion 33 itself.

The control portion 33 is configured to control the driver portion 31 and the image-processing unit 32 according to the input as the operations of the input device 5 and the images acquired by the image-processing unit 32.

According to the present embodiment, the control portion 33 has two variations of operation modes as a manual mode and an automatic mode. The control portion 33 is configured to control the driver portion 31 and the image-processing unit 32 according to one selected operation mode between the two operation modes shown above.

The manual mode is an operation mode in which the scopist operates the input device 5 to directly operate the joint 23 and the like of the arm 21 of the endoscope 2.

The automatic mode is an operation mode in which the joint 23 and the like of the arm 21 of the endoscope 2 is automatically operated by the control portion 33 according to the image acquired by the image-processing unit 32 so as to perform the automatic adjustment of the field of view of the endoscope 2.

Figure 3A:
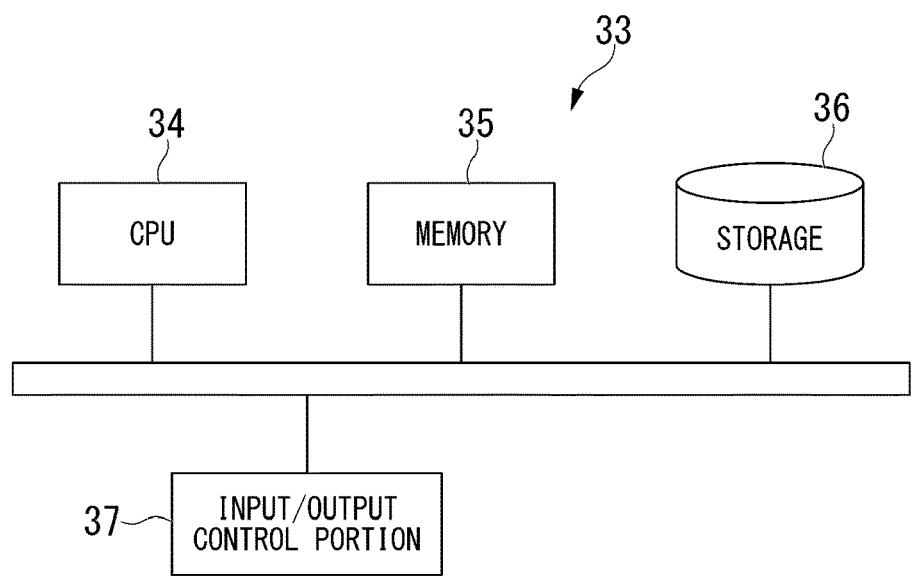
FIG. 3A is a view showing an overall configuration example of a control portion of the medical system.
Figure 3B:
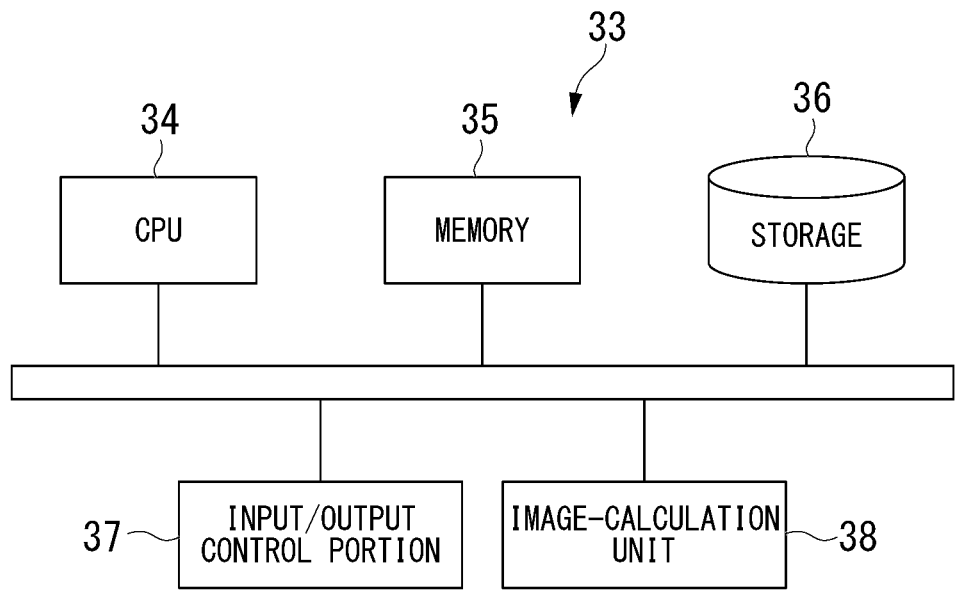
FIG. 3B is a view showing the overall configuration example of the control portion of the medical system.

FIG. 3A and FIG. 3B are views showing the overall configuration of the control portion 33.

As shown in FIG. 3A, the control portion 33 is an apparatus (computer) configured to be able to execute program, wherein the control portion 33 is configured to have a Central Processing Unit (CPU) 34, a memory 35 configured to be able to read program, a storage 36, and an input/output control portion 37.

The functions of the control portion 33 are realized by the CPU 34 executing the program provided to the control portion 33. Also, at least part of the functions of the control portion 33 may be realized by exclusive logic circuits and the like.

The storage 36 is a nonvolatile recording medium configured to store the above-mentioned program and the necessary data. For example, the storage 36 is configured by a ROM, a hard disk and the like. The program stored in the storage 36 is read by the memory 35 and then executed by the CPU 34.

The input/output control portion 37 is configured to receive the input data from the input device 5 and the image-processing unit 32 and perform the transmission of the data to the CPU 34 and the like. The input/output control portion 37 is configured to generate the control signal with respect to the driver portion 31 and the image-processing unit 32 according to the instructions from the CPU 34 when the CPU 34 takes control of the driver portion 31 and the image-processing unit 32.

Here, the control portion 33 is not limited to the apparatus provided in a single hardware. For example, the control portion 33 may be configured to have the CPU 34, the memory 35, the storage 36, and the input/output control portion 37 separated to different hardware and make the different hardware to be connected via the communication line. Also, the control portion 33 may be realized as a cloud system by separating the storage 36 and connecting the storage 36 via the communication line.

Here, the image-processing unit 32 may use the memory 35 of the control portion 33 to temporarily store the data under processing during the process of the captured image. The whole or part of the processing to the captured image by the image-processing unit 32 may be performed by the CPU 34 of the control portion 33 executing the program.

Furthermore, the control portion 33 may have other necessary configurations besides the CPU 34, the memory 35, the storage 36, and the input/output control portion 37 shown in FIG. 3A. For example, as shown in FIG. 3B, the control portion 33 may further have an image-calculation unit 38 configured to perform the whole or part of particular image processing or image recognition processing. The control portion 33 may process the particular image processing or image recognition processing rapidly by further having the image-calculation unit 38.

The display apparatus 4 is an apparatus configured to display the display image generated by the image-processing unit 32. The display apparatus 4 can be configured from the conventional display apparatus such as an LCD display and the like. The display apparatus 4 may be a head mounted display or a projector.

As shown in FIG. 2, the input device 5 has an operation input portion 51, a mode-selection unit 52, and an activate portion 53. The input device 5 is a device configured to input necessary information for the operation of the medical system 100.

The operation input portion 51 is a device configured to input the operation of the joint 23 of the arm 21 of the endoscope 2. In the situation where the imaging portion 22 has the zoom function, the operation input portion 51 can also operate the zoom function of the imaging portion 22.

Also, in the situation where the insertion portion 20 of the endoscope 2 has the active bending portion, the operation input portion 51 can make the active bending portion to bend. The scopist operates the operation input portion 51 to operate the joint 23 and the like of the arm 21.

As shown in FIG. 1, the operation input portion 51 may be configured by a joystick, or a touch panel, or an operation input device having an arm shape similar to that of the arm 21. The display apparatus 4 such as the LCD display and the operation input portion 51 such as the touch panel may be integrally configured.

By operating the operation input portion 51, the operation content is transmitted to the control portion 33. The control portion 33 is configured to calculate the movement amount of the joint 23 of the arm 21 corresponding to the operation content. The control portion 33 is configured to control the driver portion 31 so as to operate the joint 23 by the calculated movement amount.

In the situation where the operation mode of the control portion 33 is the manual mode, the joint 23 and the like of the arm 21 of the endoscope 2 are directly operated due to the operation of the operation input portion 51.

On the other hand, in the situation where the operation mode of the control portion 33 is the automatic mode, the operation of the operation input portion 51 is deactivated by the control portion 33 such that the joint 23 and the like of the arm 21 of the endoscope 2 cannot be operated. The joint 23 and the like of the arm 21 of the endoscope 2 is operated by the control portion 33.

The mode-selection unit 52 is a device configured to select an either operation mode for operating the control portion 33 between the two operation modes of the control portion 33. The mode-selection unit 52 may be configured from a switch or a touch panel. The mode-selection unit 52 may be integrally configured with the operation input portion 51. The operation-mode selection of the control portion 33 by the mode-selection unit 52 can be performed anytime.

The activate portion 53 is an activate device configured to activate the processing to make the control portion 33 to recognize the position of "region-of-interest of the surgeon" as a reference position P (hereinafter referred to "reference-position recognition processing"), and the processing to make the endoscope 2 to trace the reference position P (hereinafter referred to "reference-position tracing processing"). For example, the activate portion 53 is configured as a button switch which can switch ON/OFF of the input. The control portion 33 is configured to activate the "reference-position recognition processing" and the "reference-position tracing processing" when the input of the activate portion 53 is switched ON.

As shown in FIG. 1, the activate portion 53 according to the present embodiment is disposed at the operation portion 11 of the treatment device 1. The surgeon can control the activation and stoppage of the "reference-position recognition processing" and the "reference-position tracing processing" by switching ON/OFF of the input of the activate portion 53 with single hand while holding the operation portion 11 with single hand.

Here, the activate portion 53 may be a foot switch or a device to which the input operation by a voice can be performed. It is desirable that the activate portion 53 is configured to be able to switch ON/OFF of the input without interrupting the treatment by the surgeon using the treatment device 1.

Next, the operation of the medical system 100 and the operation method thereof will be described referring to FIG. 4 to FIG. 11, using the example of the laparoscopic surgery.

Figure 4:
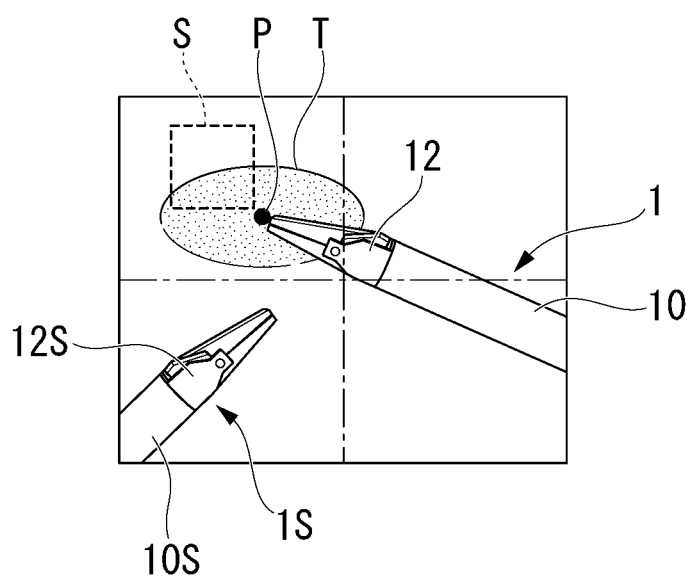
FIG. 4 is a view showing a display image of the medical system.
Figure 5:
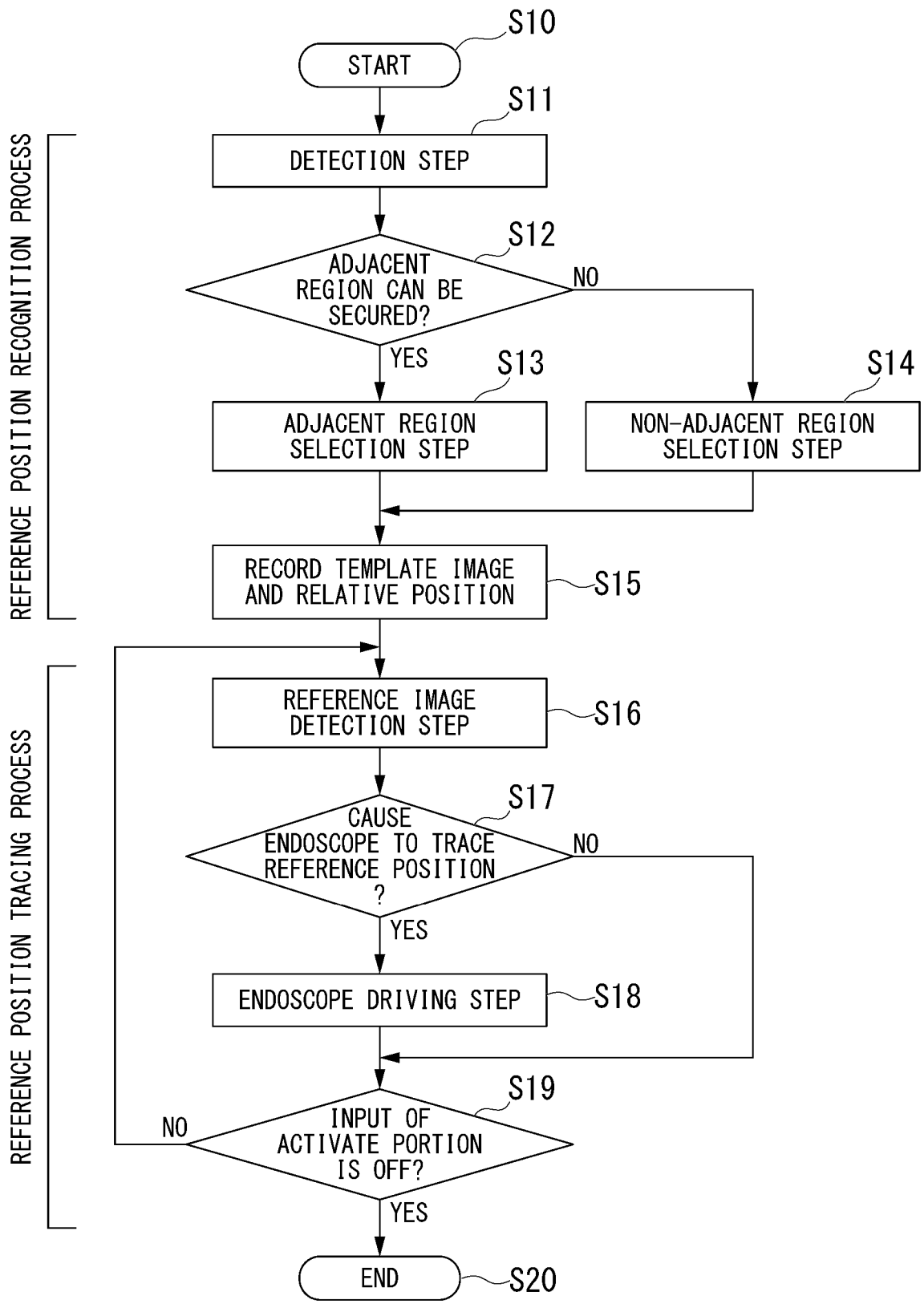
FIG. 5 is a control flowchart of the control portion in an automatic mode of the medical system.

FIG. 4 is a view showing the display image of the endoscope 2 of the medical system 100. FIG. 5 is a flowchart showing the control flow of the "reference-position recognition processing" and the "reference-position tracing processing" of the control portion 33 under the automatic mode.

The surgeon opens a plurality of holes (opening) on the abdominal area of the patient for disposing the trocar and penetrates the trocar through the holes. Next, the surgeon inserts the insertion portion 10 of the treatment device 1 through the trocar penetrating the abdominal area of the patient so as to introduce the insertion portion 10 into the body (abdominal cavity).

Furthermore, as shown in FIG. 4, the surgeon inserts an insertion portion 10S of an assistance treatment device 1S through the trocar penetrating the abdominal portion of the patient so as to introduce the insertion portion 10S into the body (abdominal cavity). Here, the assistance treatment device 1S has the same configuration with the treatment device 1 and has the insertion portion 10S with the treatment portion 12S and the operation portion 11S. The insertion portion 10S has the same configuration with that of the insertion portion 10, the operation portion 11S has the same configuration with that of the operation portion 11, and the treatment portion 12S has the same configuration with that of the treatment portion 12.

Next, the scopist operates the mode-selection 52 to set the operation mode of the control portion 33 to the manual mode. The scopist operates the operation input portion 51 to operate the endoscope 2 so as to insert the insertion portion 20 of the endoscope 2 through the trocar penetrating the abdominal portion of the patient and introduce the insertion portion 20 of the endoscope 2 into the body (abdominal cavity). Furthermore, as shown in FIG. 4, the scopist operates the operation input portion 51 to operate the endoscope 2 such that the treatment portion 12 can be captured by the imaging portion 22.

As shown in FIG. 4, in order to treat the treatment target portion T shown in the upper-left region of the display image, the surgeon would like to operate the endoscope 2 so as to make the treatment target portion T to be positioned at the center of the display image (target position). Thus, the surgeon or the scopist operates the mode-selection unit 52 to change the operation mode of the control portion 33 to the automatic mode. The operation of the operation input portion 51 is deactivated by the control portion 33 such that the scopist cannot operate the joint 23 and the like of the arm 21 of the endoscope 2.

As shown in FIG. 4, the surgeon moves the distal end of the treatment device 1 (reference position designation portion) for designating the reference position to a position in the vicinity of the center of the treatment target portion T. The surgeon turns on the input of the activate portion 53 in a state where the distal end of the treatment device 1 points to and indicates the position in the vicinity of the center of the treatment target portion T. The control portion 33 is configured to activate the "reference-position recognition processing" and the "reference-position tracing processing" when the input of the activate portion 53 is turned on. Hereinafter, description will be made following the control flowchart of the "reference-position recognition processing" and the "reference-position tracing processing" under the automatic mode as shown in FIG. 5.

As shown in FIG. 5, when the operation mode of the control portion 33 is under the automatic mode and the input of the activate portion 53 is turned on, the control portion 33 is configured to start the control of the "reference-position recognition processing" (Step S10). Next, the control portion 33 proceeds to execute Step S11.

During Step S11, as shown in FIG. 5, the control portion 33 determines (detects) the current position of the treatment device 1 from the display image at the time of the activate instruction (detection step). The control portion 33 is configured to perform the matching process between the image data of the treatment portion 12 that is stored in the storage 36 in advance and the display image at the time of the activate instruction so as to determine (detect) the position of the treatment portion 12. The matching process can be performed by selecting a suitable method from the conventional template matching methods.

In the situation where the control portion 33 has the image-calculation unit 38 configured to rapidly perform the whole or part of the image matching process, the matching process can be rapidly performed. Also, it is possible to reduce the detection time of the position of the treatment device 1 by applying a pattern or an optical marker suitable for the image matching process on the treatment portion 12.

The control portion 33 is configured to determine the positions of the treatment device 1 and the assistance treatment device 1S. The treatment portion 12 and the treatment portion 12S are applied with different colors, patterns, or optical markers such that the control portion 33 can distinguish and recognize the treatment device 1 from the assistance treatment device 1S.

In Step S11, the determined position of the distal end of the treatment device 1 is recorded in the memory 35 as the "reference position P". The recorded reference position P is a two-dimensional coordinate value in the display image at the time of the activate instruction. Here, the reference position P is not limited to one pixel, and the reference position P may be a circular arc area having an outer diameter about 10 pixels.

The area occupied by the treatment device 1 and the assistance device 1S in the display image at the time of the activate instruction is recorded as an "excluded region" in the memory 35. The excluded region refers to all of the pixels indicating the treatment device 1 and the assistance device 1S in the display image at the time of the activate instruction. The reference position P is set to the position which is not included in the excluded region.

Next, the control portion 33 proceeds to execute Step S12.

In Step S12, the control portion 33 determines whether the "template image (reference image)" adjacent to the reference position P can be secured. The control portion 33 is configured to determine whether at least one region (adjacent region), wherein the adjacent region is adjacent to the reference position P and formed by a predetermined number of pixels, can be secured from the region defined by excluding the excluded region from the whole region of the display image at the time of the activate instruction. Here, the adjacent region may include the pixel of the reference position P.

For example, in the situation where the display image is formed by 1024 pixels at the horizontal direction and 768 pixels at the vertical direction, the adjacent region is a square region formed by 64 pixels at the horizontal direction and 64 pixels at the vertical direction. The adjacent region may be a rectangle region or a circular region.

Figure 6:
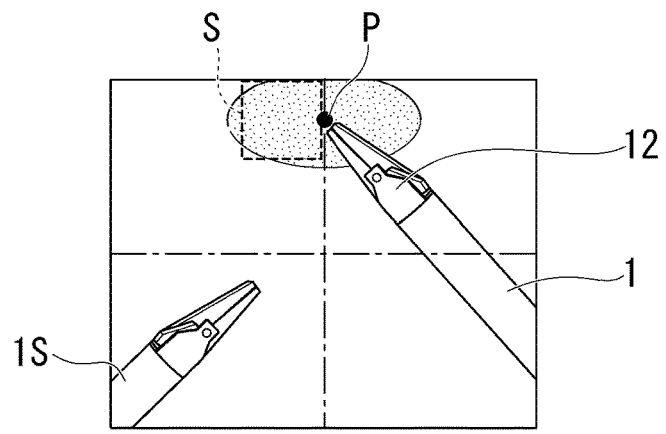
FIG. 6 is a view showing a display image of the medical system.

For example, as shown in FIG. 6, in the situation where there is no excluded region at the left side of the reference position P and at least one adjacent region can be secured, the control portion 33 determines that "the adjacent region can be secured" in the determination step.

In the situation where it is determined that the adjacent region can be secured, the control portion 33 proceeds to execute Step S13.

Figure 7:
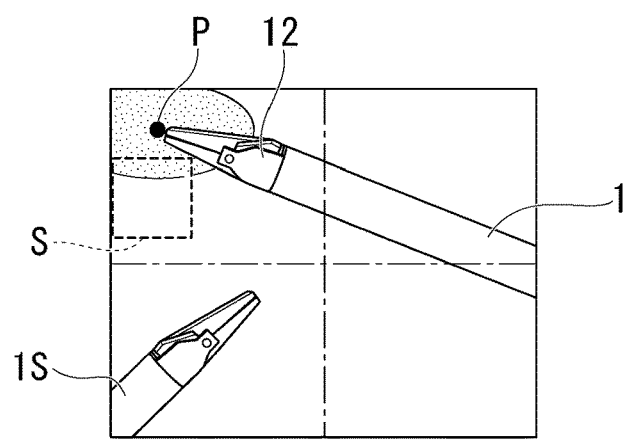
FIG. 7 is a view showing a display image of the medical system.

On the other hand, as shown in FIG. 7, in the situation where the reference position P is at the position at the upper-left side of the display image at the time of the activate instruction, the reference position P is surrounded by the excluded region that is defined by the treatment portion 12 and the corner of the display image at the time of the activate instruction such that it is impossible to secure at least one adjacent region. In this situation, the control portion 33 determines that "the adjacent region cannot be secured" in the determination step.

Figure 8:
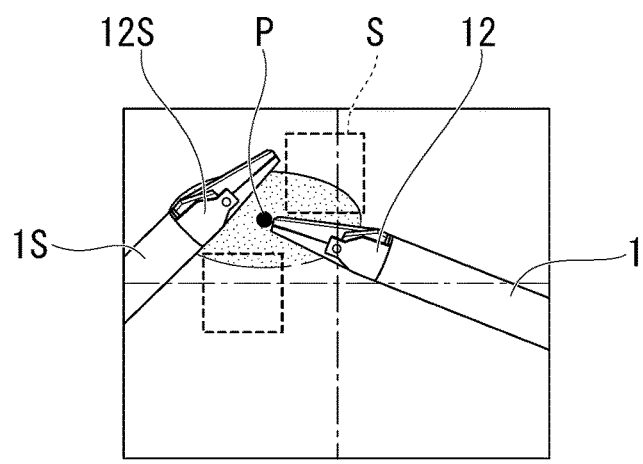
FIG. 8 is a view showing a display image of the medical system.

Also, as shown in FIG. 8, in the situation where the treatment portion 12 and the treatment portion 12S approach to each other around the reference position P such that the excluded region surrounding the reference position P is wide, it is impossible to secure at least one adjacent region. Also in this situation, the control portion 33 determines that "the adjacent region cannot be secured" in the determination step.

In the situation where it is determined that the adjacent region cannot be secured, the control portion 33 proceeds to execute Step S14 next.

During Step S13, the control portion 33 selects an adjacent region as a template image selection region S. The control portion 33 is configured to select an adjacent area which is defined to have the largest minimum-distance from the center of the selected adjacent region to the excluded region as the template image selection region S (adjacent region selection step).

For example, as shown in FIG. 4, in the situation where the treatment portion 12 as the excluded region is positioned at the lower-right side of the reference position P, the adjacent region at the opposite side with respect to the treatment portion 12 across the reference position P is the adjacent region from which the minimum-distance to the excluded region is the largest. Accordingly, this adjacent region is selected as the template image selection area S.

For example, as shown in FIG. 6, in the situation where the reference position P is positioned at the upper side of the display image at the time of the activate instruction and the treatment portion 12 as the excluded region is positioned at the right side of the reference position P, the adjacent region at the opposite side with respect to the treatment portion 12 across the reference position P is the adjacent region from which the minimum-distance to the excluded region is the largest. Accordingly, this adjacent region is selected as the template image selection area S.

Next, the control portion 33 proceeds to execute Step S15.

In Step S14, the control portion 33 is configured to select the "template image" which is not adjacent to the reference position P. The control portion 33 is configured to select a non-adjacent region as the template image selection region S, wherein the non-adjacent region is defined as a region (non-adjacent region) which is not adjacent to the reference position P and formed by a predetermined number of pixels from the region defined by excluding the excluded region from the whole region of the display image at the time of the activate instruction. The control portion 33 is configured to select a non-adjacent area which is defined to have the smallest minimum-distance from the center of the selected non-adjacent region to the reference position P as the template image selection region S (non-adjacent region selection step).

There are a lot of non-adjacent regions existing such that it is not necessary to list up all of the candidates before the selection. For example, the control portion 33 can select the non-adjacent region that has the smallest minimum-distance from the center of the selected non-adjacent region to the reference position P by discovering the non-adjacent region in a spiral direction in a sequence from the region near the reference position P.

For example, as shown in FIG. 7, the non-adjacent region at the lower side of the reference position P which is not adjacent to the reference position P is selected as the template image selection region S.

Also, as shown in FIG. 8, the non-adjacent region at the upper-right side of the reference position P which is not adjacent to the reference position P is selected as the template image selection region S.

Next, the control portion 33 proceeds to execute Step S15.

In Step S15, the control portion 33 is configured to record the image of the template image selection region S as the "template image (reference image)" in the memory 35. The control portion 33 is configured to calculate the relative position of the reference position P with respect to the two-dimensional coordinate of the center SO of the selected template image selection region S and record the calculated relative position in the memory 35.

Figure 9:
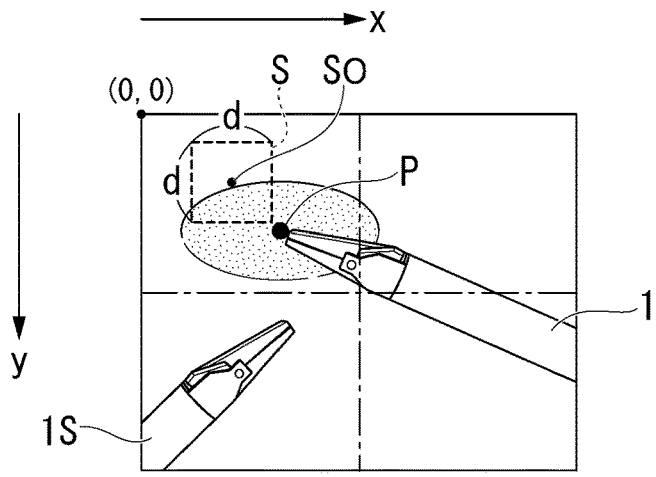
FIG. 9 is a view showing a display image of the medical system.

FIG. 9 is a display image showing the selected template image selection region S. In the display image, the origin is located at the upper-left side, the horizontal axis is shown as X-axis, the vertical axis is shown as Y-axis, and the coordinate in the display image having x component on the X-axis and y component on the Y-axis is shown as (x, y).

In the example shown in FIG. 9, the adjacent region which is adjacent to the reference position P at the upper-left side is selected as the template image selection region S. In this situation, when the template image selection region S is defined as the square region having a side length of d pixels, the relative position of the reference position P with respect to the center SO of the template image selection region S is (d/2, d/2).

Next, the control portion 33 proceeds to execute Step S16. After Step S16, the control portion 33 starts controlling the "reference-position tracing process" of the endoscope 2.

In Step S16, the control portion 33 is configured to perform the template matching process with respect to the display image after the time of the activate instruction using the template image recorded during Step S15, and the control portion 33 is configured to determine the coordinate of the center DO of the image region (template image detection region D), wherein it is determined that the template image is included in the image region (template image detection region D) (reference image detection step). The matching process is performed by using a suitable method selected from the conventional template matching methods.

The control portion 33 is configured to calculate the current position of the reference position P from the coordinate of the center DO of the template image detection region D according to the relative position of the reference position P.

Figure 10:
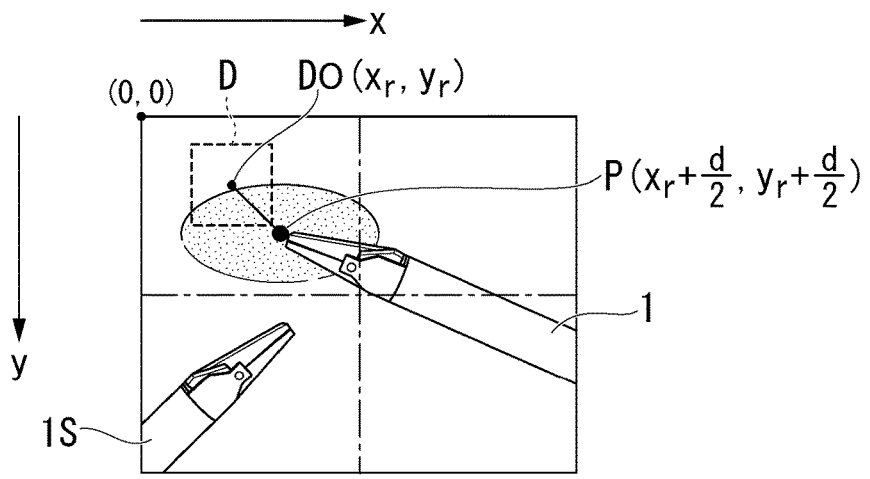
FIG. 10 is a view showing a display image of the medical system.

FIG. 10 is a display image showing the determined template image detection region D.

At the time of selecting the template image during Step S15, since the relative position of the reference position P with respect to the center SO of the template image selection region S is (d/2, d/2), the relative position of the reference position P with respect to the coordinate (Xr, Yr) of the center DO of the template image detection region D is also (d/2, d/2). Accordingly, as shown in FIG. 10, the coordinate of the current reference position P is (Xr+d/2, Yr+d/2).

Next, the control portion 33 proceeds to execute Step S17.

In the situation where Step S16 is performed immediately after Step S15, the template matching process can be omitted, and the "selected template image selection region S" recorded in Step S15 may be regarded as the "determined template image detection region D" in Step S16. Since the period from Step S15 to Step S16 is short, the possibility that the template image selection region S and the template image detection region D become different regions due to the movement of the organs and tissues in the abdominal cavity occurred by the breathe of the patient is low.

In Step S17, the control portion 33 is configured to determine whether it is necessary to make the endoscope 2 to trace the reference position P such that the endoscope 2 is moved to make the reference position P at the center (target position) of the display image.

In the situation where the coordinate (Xr+d/2, Yr+d/2) of the reference position P coincides with the center (target position) of the display image, it is determined that it is not necessary to make the endoscope 2 to trace the reference position P. Here, at the situation of determining whether the coordinates coincide with each other, the coordinates may be determined to coincide with each other even there is a difference of about 10 pixels. Also, the difference of pixels may be suitably set.

In the situation where it is determined that it is not necessary for the endoscope 2 to trace the reference position P, the control portion 33 proceeds to execute next Step S19.

On the other hand, as shown in FIG. 10, in the situation where the coordinate of the reference position P (Xr+d/2, Yr+d/2) does not coincide with the center of the display image (target position), it is determined that it is necessary to make the endoscope 2 to trace the reference position P.

In the situation where it is determined that it is necessary to make the endoscope 2 to trace the reference position P, next, the control portion 33 proceeds to execute Step S18.

In Step S18, the control portion 33 causes the endoscope 2 to trace the reference position P such that the coordinate of the reference position P (Xr+d/2, Yr+d/2) coincides with the center of the display image (target position). The control portion 33 is configured to calculate the movement amount of the joint 23 of the arm 21 from the coordinate of the reference position P on the display image and the coordinate of the center (target position) of the display image. The control portion 33 is configured to control the driver portion 31 to drive the joint 23 (endoscope driving step).

Here, the control portion 33 may determine the maximum movement amount of the reference position P. In Step S17, during the period when the control portion 33 operates the endoscope 2 to make the reference position P to approach the center of the display image (target position), in the situation where the movement amount of the reference position P reaches the maximum movement amount, the control portion 33 stops the operation of the endoscope 2 and proceeds to execute Step S19. In other words, in this situation, at the end of Step S18, the coordinate of the reference position P does not coincide with the coordinate of the center of the display image (target position). The control portion 33 is configured to make the coordinate of the reference position P and the coordinate of the center of the display image (target position) to coincide with each other by executing the process from Step S16 to Step 18 for several times.

If the maximum movement amount of the reference position P is determined, for example, in the situation where the reference position P and the display of the display image (target position) are much apart from each other, it is possible to prevent the display image from changing suddenly since the endoscope 2 moves widely at once.

In Step S18, during the period when the endoscope 2 is operated, due to the movement of the organs and tissues in the body (abdominal cavity) caused by the breathe of the patient, there may be a situation where the reference position P recognized by the control portion 33 does not coincide with the position which should be recognized as the reference position P. By executing the process from Step S16 to Step 18 for several times to make the coordinate of the reference position P to coincide with the coordinate of the center of the display image (target position), even in the above-described situation, it is possible to make the position which should be recognized as the reference position to coincide with the center of the display image (target position).

In Step S19, the control portion 33 is configured to confirm the input of the activate portion 53, and in the situation where the input is turned off, the control portion executes Step S20 to terminate the control of the "reference position tracing process". If the input is still turned on, the control portion 33 subsequently executes Step S16 again.

Figure 11:
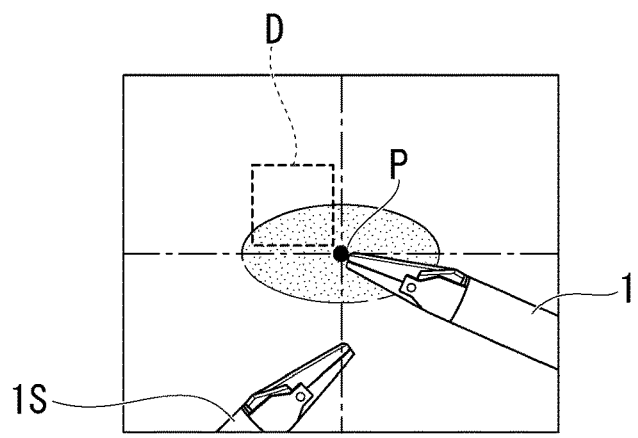
FIG. 11 is a view showing a display image of the medical system.

FIG. 11 is a view showing that the reference position P coincides with the center of the display image (target position). The control portion 33 can make the reference position P to coincide with the center of the display image (target position) by executing the process from Step S16 to Step S18 for several times.

The surgeon can turn off the input off the activate portion 53 to terminate the control of the "reference position tracing process" when the surgeon performs treatment with respect to different treatment target region. The surgeon moves the distal end of the treatment device 1 (reference position designation portion) to a position indicating the vicinity of the center of a new treatment target region and turns on the input of the activation portion 53 again. The control portion 33 is configured to start the "reference-position recognition processing" and the "reference-position tracing processing" by regarding the position indicated by the distal end of the treatment device 1 (reference position designation portion) as a new reference position P.

Effect of First Embodiment

According to the medical system 100 of the present embodiment, the endoscope 2 is automatically operated to make the reference position P instructed by the surgeon to be at the center of the display image (target position) such that the most suitable field of view of the endoscope 2 for the treatment can be provided. The image in which the designated region-of-interest is included rather than the image provided by always tracing the distal end of the treatment device 1.

In the medical system 100 according to the present embodiment, it is possible to recognize the reference position P instructed by the surgeon at the relative position from the position where the template image (reference image) is determined to be included, such that it is easy to recognize the reference position P and trace the reference position P by using the image processing.

In the medical system according to the present embodiment, the region where the treatment device and the like are shown so as to be not suitable for specifying the reference position P is defined as the excluded region, and the template image (reference image) is selected from the region excluding the excluded region. Accordingly, it is possible to determine the template image (reference image) so as to definitely specify the reference position P instructed by the surgeon.

In the medical system 100 according to the present embodiment, the contact region adjacent to the reference position P is preferably selected as the template image selection area S. Accordingly, for example, even in the situation in which the endoscope 2 is moved such that the angle of the field of view of the endoscope is changed, it is easy to maintain the matching precision of the template matching process.

In the medical system 100 according to the present embodiment, even in the situation in which the contact region adjacent to the reference position P cannot be preferably selected as the template image selection area S, the non-contact region can be selected as the template image selection area S.

In the medical system according to the present embodiment, it is possible to prevent the field of view in the display image from being suddenly changed by designating the maximum movement amount of the reference position P during one operation of the endoscope 2.

Modification Example

Hereinbefore, the first embodiment of the present invention has been described above in detail with reference to the drawings, the specific configuration is not limited to this embodiment, but also includes changes in design and the like without departing from the scope of the present invention. Modifications of the above-mentioned embodiment are given below. Also, the configuration elements according to the above-described first embodiment and the modification examples shown below can be suitably combined.

In the above-described embodiment, the display image is changed by operating the arm of the endoscope to change the imaging position of the endoscope, however, the method of changing the display image is not limited thereto. The image-processing unit may have the function of cutting out a partial region of the capture image of the endoscope to generate the display image, and the image-processing unit may change the display image by changing the position of cutting out the image. It is also possible to change the display image for an endoscope without any arm.

Figure 12:
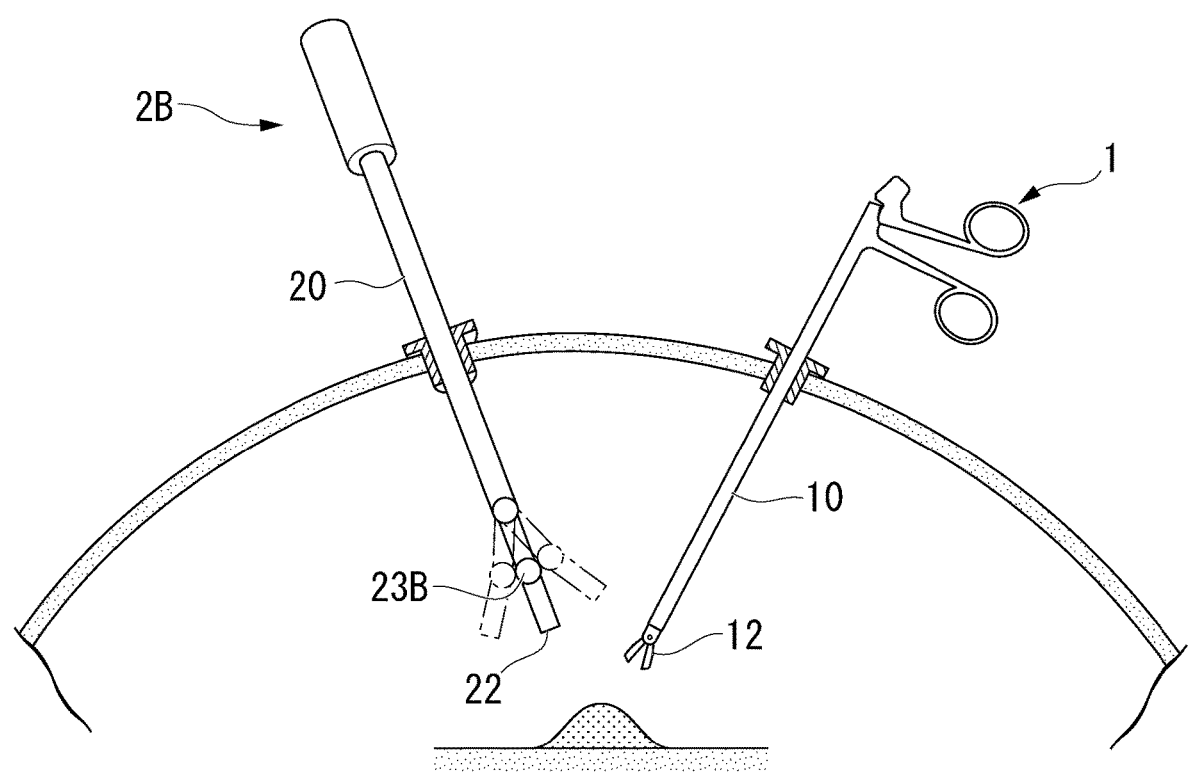
FIG. 12 is a view showing an overall configuration of a modification example of the endoscope of the medical system.

FIG. 12 is a view showing an overall configuration example of an endoscope 2B as a modification example of the endoscope 2. The endoscope 2B has an active bending portion 23B at a distal end of the insertion portion 20. The surgeon can change the position and the orientation of the imaging unit 22 of the endoscope 2B by holding and moving the endoscope 2B. Also, the surgeon can change the position and the orientation of the imaging unit 22 by bending the active bending portion 23B.

Instead of the endoscope 2, in the situation of using the endoscope 2B, the control portion 33 can change the display image by driving the active bending portion 23B.

According to the above-described embodiment, the reference position designation portion configured for the surgeon to designate the reference position P is provided at the distal end of the treatment portion 12, however, the reference position designation portion is not limited thereto. The reference position designation port ion may be the distal end of the treatment device having a high-frequency knife instead of a pair of grasping members 12a.

Also, in the situation where the LCD display as the display apparatus 4 and the touch panel as the operation input unit 51 are integrally configured, the designation of the reference position may be performed by using the input to the touch panel.

According to the above-described embodiment, the excluded region is regarded as the region occupied by the treatment device 1 and the assistance treatment device 1S shown in the display image, however, the excluded region is not limited thereto. The region where some object, whose relative position with respect to the reference position P cannot be determined such as "the obstacle including the blood and contaminant attached to the imaging unit of the endoscope" and "object used for the treatment including the gauze and the like", is shown can be further determined as the excluded region. It is possible to determine the template image (reference image) so as to more definitely specify the reference position P instructed by the surgeon.

According to the above-described embodiment, the endoscope 2 is automatically operated so as to make the reference position P to be at the center of the display image (target position), however, the position tracing the reference position P (target position) is not limited to be in the center of the display image. The target position may be at a position other than the center of the display image. For example, in the situation where the display apparatus 4 is configured from two LCD monitors, the center of the display image on either monitor may be determined as the target position.

According to the above-described embodiment, the control portion 33 is configured to select the non-adjacent region which is defined to have the smallest minimum-distance from the center of the selected non-adjacent region to the reference position P as the template image selection region S, however, the method of selecting the template image selection region S from the non-adjacent region is not limited thereto. The control portion 33 may select a non-adjacent region which is defined to have a small minimum-distance from the center of the selected non-adjacent region to the reference position P while having a characteristic value suitable for the template image. The precision of the template matching can be improved.

Second Embodiment

A second embodiment of the present invention will be described by referring to FIG. 13 to FIG. 15. The present embodiment is different from the first embodiment in that a plurality of template images (reference images) are selected for specifying the preference position P. In the following description, the described common configuration will be assigned to the same reference sign and the description thereof will be omitted.

An overall configuration of a medical system 200 according to the present embodiment is same with the configuration of the medical system 100 according to the first embodiment. The medical system 200 is different from the medical system 100 in the control of the "reference-position recognition processing" and the "reference-position tracing processing".

In the "reference-position recognition processing", the control portion 33 is configured to select the template image selection region S as a first template image selection region S1, and further selects a second template image selection region S2 from the non-adjacent region.

Figure 13:
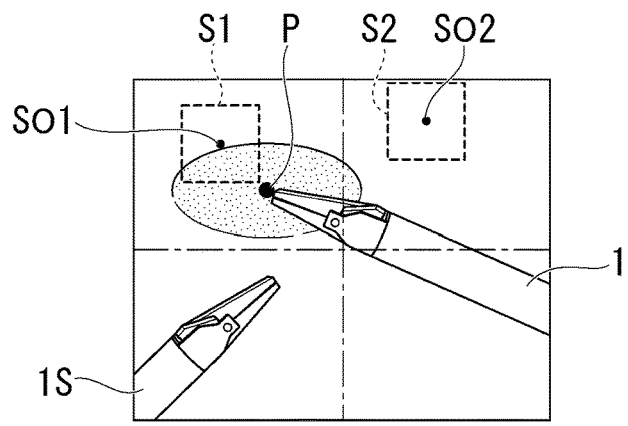
FIG. 13 is a view showing a display image of a medical system according to a second embodiment of the present invention.

FIG. 13 is a view showing the display image during the period of performing the reference-position recognition processing.

As shown in FIG. 13, the control portion 33 is configured to select one adjacent region as the first template image selection region S1 using the same method with that according to the first embodiment, in the situation where the contact area can be secured.

On the other hand, in the situation where the contact area cannot be secured, the control portion 33 is configured to select one non-adjacent region as the first template image selection region S1 using the same method with that according to the first embodiment.

The control portion 33 is configured to record the image of the first template image selection region S1 in the memory 35 as the "first template image (first reference image)". Also, the control portion 33 is configured to record the relative position of the reference position P with respect to the coordinate of the center SO1 of the template image selection region S1.

As shown in FIG. 13, the control portion 33 is configured to select the non-adjacent region which is defined to have the smallest minimum-distance from the center of the selected non-adjacent region to the reference position P among the plurality of non-adjacent regions being apart from the first template image selection region S1 by a predetermined distance as the second template image selection region S2.

The control portion 33 is configured to record the image of the second template image selection S2 in the memory 35 as the "second template image (second reference image)". Also, the control portion 33 is configured to record the relative position of the reference position P with respect to the coordinate of the center SO2 of the second template image selection region S2 in the memory 35.

In the "reference-position tracing processing", the control portion 33 can recognize the reference position P according to the relative position thereof from the position where it is determined that the first template image is included and trace the reference position P using the same method with that of the first embodiment. Furthermore, in the situation where it is determined that the first template image is not included in the display image during the matching process, the control portion 33 can further perform the matching process by the second template image, recognize the reference position P according to the relative position thereof from the position where it is determined that the second template image is included and trace the reference position P.

Figure 14:
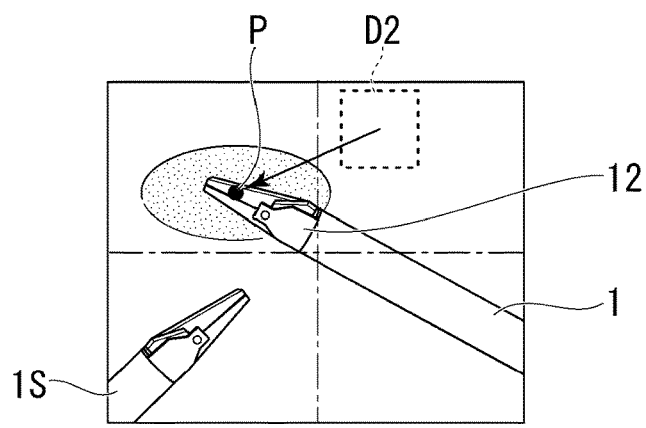
FIG. 14 is a view showing a display image of the medical system.

FIG. 14 is a view showing the display image during the period of performing the reference-position tracing processing.

As shown in FIG. 14, in the situation where the surgeon moves the treatment portion 12 and the treatment portion 12 in the display image is moved to the position superimposed to the position where the first template image is determined, the control portion 33 cannot determine that the first template image is included in the display image by the matching process.

Even in this situation, as shown in FIG. 14, the second template image (second template image detection region D2) can be determined by the matching process using the second template image. The current position of the reference position P from the center DO2 of the second template image detection region D2 can be recognized according to the relative position of the reference position P with respect to the center SO2 of the recorded second template image selection region S2.

Figure 15:
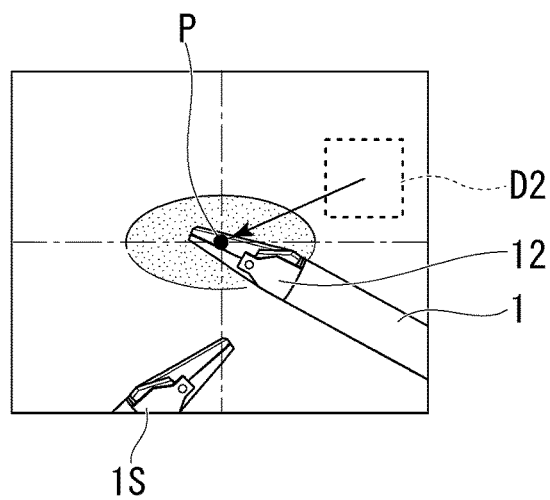
FIG. 15 is a view showing a display image of the medical system.

FIG. 15 is a view showing the display image in which the reference position P coincides with the center of the display image (target position). As shown in FIG. 15, the control portion 33 can use other template image to perform the matching process so as to recognize the reference position P and make the reference position P and the center of the display image (target position) to be coincided with each other, even in the situation where the region from which one template image is determined is displayed and superimposed by the excluded region of the treatment device 1 and the like.

Effect of Second Embodiment

In the medical system 200 according to the present embodiment, even in the situation where the region from which one template image is determined is displayed and superimposed by the excluded region of the treatment device 1 and the like, by performing the matching process using other template image, it is possible to recognize the reference position P and make the reference position P and the center of the display image (target position) to be coincided with each other.

In the medical system 200 according to the present embodiment, even in the situation where the surgeon performs the treatment to the treatment target region T and the shape of the treatment target region T is changed such that one template image cannot be determined, by using other template image to perform the matching process, the reference position P can be recognized and the reference position P and the center of the display image (target position) can be made to be coincided with each other.

Modification Example

Hereinbefore, the second embodiment of the present invention has been described above in detail with reference to the drawings, the specific configuration is not limited to this embodiment, but also includes changes in design and the like without departing from the scope of the present invention. Modifications of the above-mentioned embodiment are given below. Also, the configuration elements according to the above-described second embodiment and the modification examples shown below can be suitably combined.

According to the above-described embodiment, the number of used template images is two, however, the number of the template images is not limited thereto. The number of template images may be equal to or larger than three. By selecting a plurality of template images so as to equally arrange the plurality of template images in the circumferential direction around the reference position P, it is possible to suitable prevent all of the plurality of template images being displayed in a manner of superimposing on the excluded region of the treatment device 1 and the like.

Third Embodiment

A third embodiment of the present invention will be described by referring to FIG. 16. The present embodiment is different from the first embodiment in that the template image is updated. In the following description, the described common configuration will be assigned to the same reference sign and the description thereof will be omitted.

An overall configuration of a medical system 300 according to the present embodiment is same with the medical system 100 according to the first embodiment. The medical system 300 is different from the medical system 100 in the control of the "reference position tracing processing". When it is determined that the reference position P and the center of the display image (target position) are coincided with each other, the medical system 300 is configured to determine whether the template image can be updated.

Figure 16:
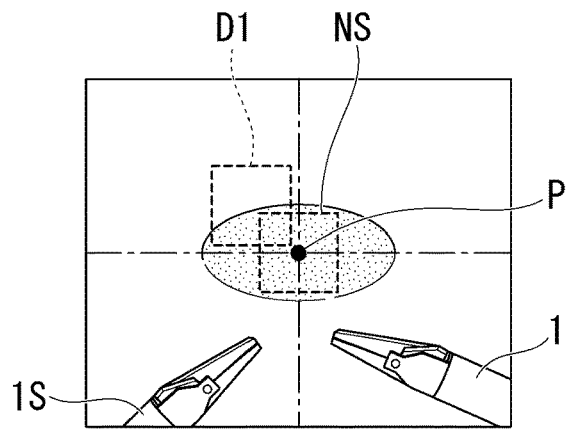
FIG. 16 is a view showing a display image of a medical system according to a third embodiment of the present invention.

FIG. 16 is a view showing the display image in which the reference position P and the center of the display image (target position) are coincided with each other during the "reference position tracing processing".

After the reference position P and the center of the display image (target position) are determined to be coincided with each other, in the situation where there is no excluded region in the circumference of the reference position P, the control portion 33 is configured to select a region which is defined to have a center more closer to the reference position P as a new template image selection region NS and update the template image.

For example, as shown in FIG. 16, the region in which the position of the center thereof coincided with the reference position P can be selected as the new template image selection region NS.

Effect of Third Embodiment

In the medical system 300 according to the present embodiment, the treatment target portion T which is desired to be traced can be much included in the template image so as to improve the precision of the matching process.

Fourth Embodiment

A fourth embodiment of the present invention will be described by referring to FIG. 17 and FIG. 18. The present embodiment is different from the second embodiment in that the template image is updated. In the following description, the described common configuration will be assigned to the same reference sign and the description thereof will be omitted.

An overall configuration of a medical system 400 according to the present embodiment is same with the configuration of the medical system 200 according to the second embodiment. The medical system 400 is different from the medical system 200 in the control of the "reference position tracing processing". The control portion 33 is configured to determine whether the update of the first template image is possible when the first template image is determined not to be included in the display image during the matching process.

Figure 17:
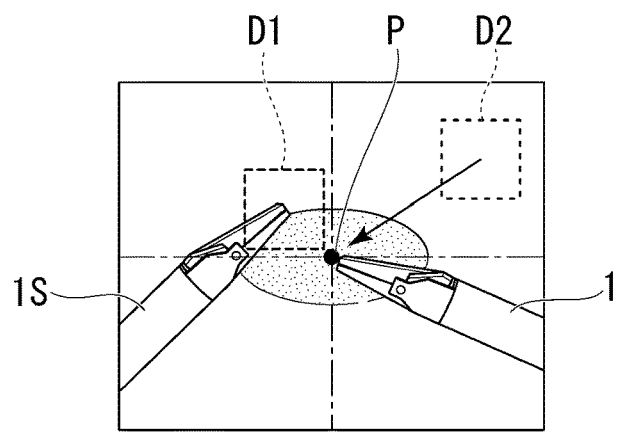
FIG. 17 is a view showing a display image of a medical system according to a fourth embodiment of the present invention.

FIG. 17 is a view showing the display image during the "reference position tracing processing". As shown in FIG. 17, the control portion 33 determines that the first template image is not included in the display image, determines the second template display image, and recognizes the reference position P from the position of the second template image detection region D2.

In the next reference-position tracing processing from the positions of the treatment device 1 and the assistance treatment device 1S, the possibility that the first template image cannot be determined is high. Thus, the update of the first template image is performed.

Figure 18:
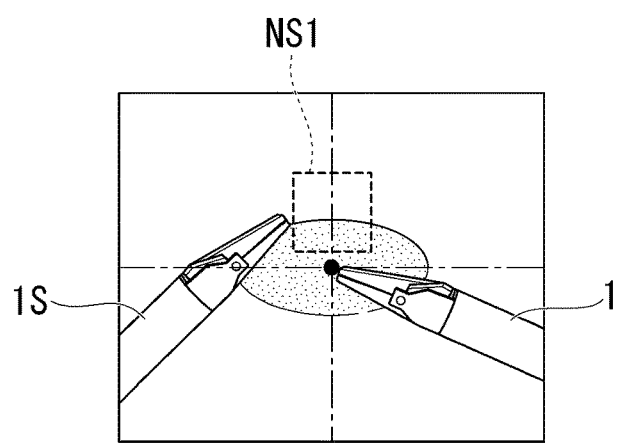
FIG. 18 is a view showing the display image of the medical system.

FIG. 18 is a view showing the display image when the update of the template image is performed.

The control portion 33 is configured to select the template image region in the same manner with the reference-position recognition processing according to the first embodiment. As shown in FIG. 18, the selected template image region is selected as the new template image selection region NS1 and updated as the first template image.

Effect of Fourth Embodiment

In the medical system 400 according to the present embodiment, by updating the template image which cannot be determined, the situation in which all of the template image regions are displayed in the way of being superimposed by the excluded region of the treatment device 1 and the like can be suitably prevented.

Modification Example

Hereinbefore, the fourth embodiment of the present invention has been described above in detail with reference to the drawings, the specific configuration is not limited to this embodiment, but also includes changes in design and the like without departing from the scope of the present invention. Modifications of the above-mentioned embodiment are given below. Also, the configuration elements according to the above-described fourth embodiment and the modification examples shown below can be suitably combined.

According to the above-described embodiment, it is described to determine whether the first template image can be updated, however, the embodiment of updating the template image is note limited thereto. Even in the situation where the first template image is determined to be included in the display image, the matching processing may be performed using the second template image, and even in the situation where the second template image is determined not to be included in the display image, the second template image may be updated. The control portion 33 can maintain a plurality of template images so as to definitely perform the matching processing.

Fifth Embodiment

A fifth embodiment of the present invention will be described by referring from FIG. 19 to FIG. 21. The present embodiment is different from the first embodiment to the fourth embodiment in the embodiment of selecting the template image. In the following description, the described common configuration will be assigned to the same reference sign and the description thereof will be omitted.

An overall configuration of a medical system 500 according to the present embodiment is same with the configuration of the medical system 100 according to the first embodiment. The medical system 500 is different from the medical system 100 in the control of the "reference-position recognition processing". When the control portion 33 determines whether the "template image (reference image)" adjacent to the reference position P can be secured (determination step), the control portion 33 is configured to determine whether the "template image (reference image)" can be secured from the display image several seconds ago rather than the current display image.

Figure 19:
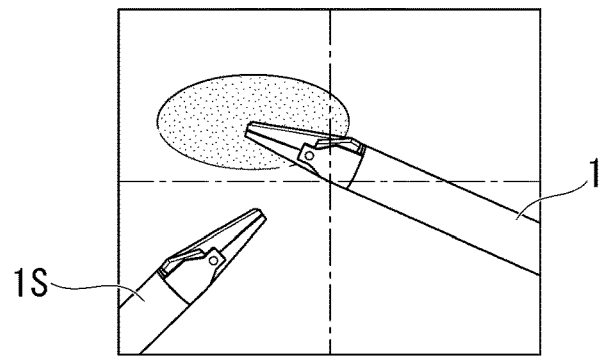
FIG. 19 is a view showing a display image of a medical system according to a fifth embodiment of the present invention.

FIG. 19 is a view showing the display image at the time when the input of the activate portion 53 is turned on and the control portion 33 performs the determination step. FIG. 20 is a view showing the display image at t1 time earlier than that of the display image in FIG. 19. FIG. 21 is a view showing the display image at t2 time earlier than that of the display image in FIG. 19.

The control portion 33 of the medical system 500 is configured to make the display images at the t1 time ago and the t2 time ago to be recorded in the memory 35.

In the determination step, since the distal end of the treatment device (preference position designation portion) is configured for indicating the reference position P, the distal end of the treatment device is in the periphery of the reference position P. Accordingly, according to the first embodiment to the fourth embodiment, the region occupied by the distal end of the treatment device 1 is regarded as the excluded region, and the template image (reference image) is selected from the region excluding the excluded region.

However, before the surgeon moves the distal end of the treatment device (preference position designation portion) to the reference position P, the possibility of the distal end of the treatment device 1 being not in the periphery of the reference position P is high.

Accordingly, when the input of the activate portion 53 is turned on, the control portion 33 determines whether the "template image (reference image)" can be secured not only from the display image at the time of the control portion 33 performing the determination step but also from the display image several seconds ago.

Figure 20:
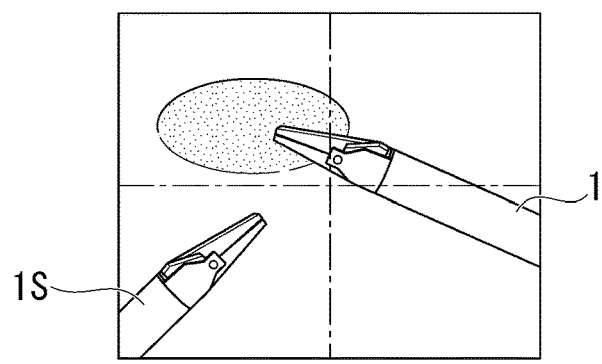
FIG. 20 is a view showing the display image of the medical system.
Figure 21:
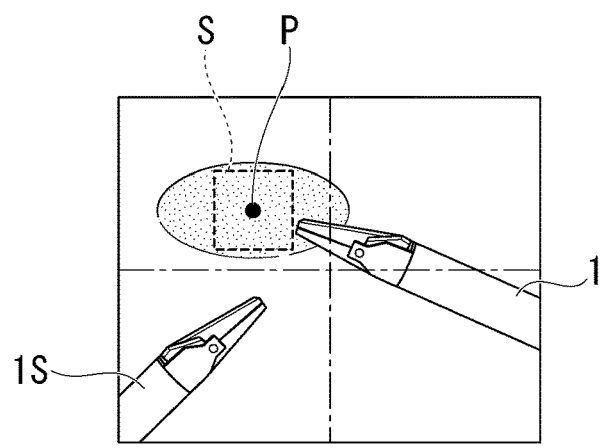
FIG. 21 is a view showing the display image of the medical system.

As shown in FIG. 19 to FIG. 21, it is disclosed that the distal end of the treatment device 1 is approaching the reference position P from the lower-right side of the display image. As shown in FIG. 21, in the display image at t2 time ago, the region in which the position of the center thereof is coincided with the reference position P can be selected as the template image selection region S.

Effect of Fifth Embodiment

In the medical system 500 according to the present embodiment, the treatment target portion T which is desired to be traced can be much included in the template image so as to improve the precision of the matching process.

Sixth Embodiment

A sixth embodiment of the present invention will be described by referring to FIG. 22 and FIG. 23. The present embodiment is different from the first embodiment to the fifth embodiment in the embodiment of selecting the template image. In the following description, the described common configuration will be assigned to the same reference sign and the description thereof will be omitted.

An overall configuration of a medical system 600 according to the present embodiment is same with the configuration of the medical system 100 according to the first embodiment. The medical system 600 is different from the medical system 100 in the control of the "reference-position tracing processing". The control portion 33 is configured to perform error processing when any one of the template image cannot be determined during the reference image detection step.

In the situation where the control portion cannot determine any one template image during the reference detection step, for example, due to the situation where the blood is attached to the imaging portion 22 of the endoscope 2, it is possible that the template matching processing cannot be suitably performed. In such a situation, if the automatic operation of the endoscope 2 is continued, operations having unfavorable effects to the treatment such as the endoscope 2 moves in an unintentional direction may occur. Thus, the control portion 33 is configured to perform the error processing.

Figure 22:
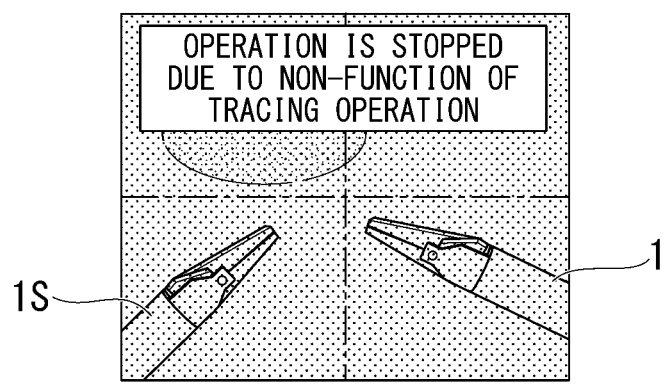
FIG. 22 is a view showing a display image of a medical system according to a sixth embodiment of the present invention.
Figure 23:
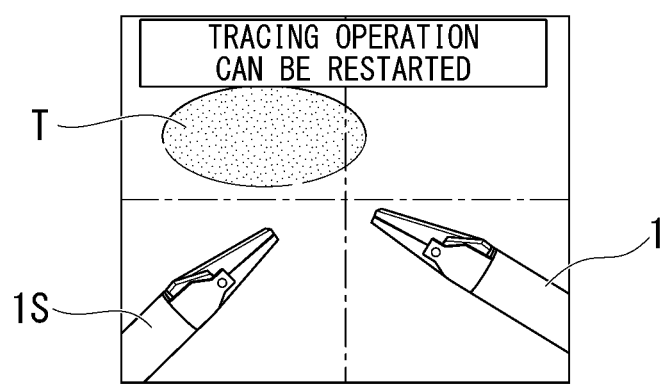
FIG. 23 is a view showing the display image of the medical system.

FIG. 22 and FIG. 23 are examples of the display image during the error processing.

For example, the control portion 33 is configured to stop the automatic operation of the endoscope 2 and notify the surgeon with the situation by displaying the error message on the display image. Also, in the situation where the surgeon wipes away the blood attached on the imaging unit 22 of the endoscope 2 and the like such that the template matching processing can be suitable performed, as shown in FIG. 23, the control portion 33 is configured to notify the surgeon with the message that the automatic operation of the endoscope 2 can be resumed by displaying the message on the display image. The surgeon can turn on the input of the activate portion 53 again to resume the automatic operation of the endoscope 2.

Effect of Sixth Embodiment

In the medical system 600 according to the present embodiment, during the reference-position tracing processing, in the situation where the tracing for the reference position P cannot be performed, the automatic operation of the endoscope 2 is stopped so as to prevent the endoscope 2 from performing unfavorable operation to the treatment. Also, it is possible to notify the surgeon with the situation where the template matching processing cannot be properly performed by displaying the error message.

Although an embodiment of the present invention has been described above in detail with reference to the drawings, the specific configuration is not limited to the embodiment, and also includes various modifications. The present invention is not limited to the aforementioned embodiment, but is only limited by the appended claims.

What is claimed is:

1. A medical system, comprising:
    a treatment device having a reference position designation portion;
    an endoscope which is electrically driven and configured to acquire a plurality of captured images;
    a storage device configured to record the plurality of captured images;
    a controller configured to generate a plurality of display images corresponding to the plurality of captured images acquired by the endoscope; and
    a display configured to display the plurality of display images,
    wherein the controller is configured to:
        determine an arbitrary position designated by the reference position designation portion in one of the plurality of display images as a reference position,
        detect a region in the display image where the treatment device is displayed as an excluded region and select a reference image with a predetermined size from a region in the display image excluding the excluded region,
        record the reference image in the storage device,
        calculate a relative position from the reference position to the reference image,
        detect the reference image from the plurality of display images after the reference image is generated, and recognize the reference position in the display image according to the position of the reference image and the relative position, and
        control an operation of the endoscope so as to make the reference position to be coincided with a target position on the display image after the reference image is generated.

2. The medical system according to claim 1, wherein the controller is configured to select an image of the adjacent region as the reference image and detect an adjacent region which is adjacent to the reference position.

3. The medical system according to claim 2, wherein the controller is configured to select an image of the adjacent region as the reference image, where a distance between a center of the selected adjacent region and the excluded region is the largest.

4. The medical system according to claim 2, wherein the controller is configured to select an image of a non-adjacent region from a plurality of non-adjacent regions being not adjacent to the reference position as the reference image, where a distance between a center of the selected non-adjacent region and the reference position is the smallest, when none of adjacent region being adjacent to the reference position can be secured.

5. The medical system according to claim 1, wherein the controller is configured to select and update the reference image when the controller determines that the reference position and the target position coincide with each other.

6. The medical system according to claim 1,
wherein the controller is configured to:
store the reference image selected from the adjacent region or the non-adjacent region in the storage device as a first reference image,
store the reference image selected from a region in the non-adjacent region where the first reference image is not included in the storage device as a second reference image, and
determine the second reference image as the reference image when the first image is not detected in any of the plurality of display images generated after the reference image is selected.

7. The medical system according to claim 1, wherein at the time of selecting the reference image from the display image after an activate instruction for activating the controller is input, the controller is configured to select the reference image from the display image before the activate instruction.

8. The medical system according to claim 1, wherein the reference position designation portion is a distal end of the treatment device.

9. The medical system according to claim 1, wherein the target position is a center of the display image.

10. An operation method of a medical system, wherein the medical system having a treatment device having a reference position designation portion, an endoscope which is electrically driven and configured to acquire a plurality of captured images, a storage device configured to record the plurality of captured images, a controller configured to generate a plurality of display images corresponding to the plurality of captured images acquired by the endoscope, and a display configured to display the plurality of display images, comprising:

a process of determining an arbitrary position designated by the reference position designation portion in one of the plurality of display images as a reference position;
a process of detecting a region in the display image where the treatment device is displayed as an excluded region and selecting a reference image with a predetermined size from a region in the display image excluding the excluded region;
a process of recording the reference image in the storage device;
a process of calculating a relative position from the reference position to the reference image;
a process of detecting the reference image from the plurality of display images after the reference image is generated and recognizing the reference position in the display image according to the position of the reference image and the relative position, and
a process of controlling an operation of the endoscope so as to make the reference position to be coincided with a target position on the display image after the reference image is generated.

11. The operation method of a medical system according to claim 10, wherein the process of determining the reference image includes a process of judging whether an adjacent region being adjacent to the reference position can be secured and determining the adjacent region.

12. The operation method of a medical system according to claim 11, wherein when it is determined that the adjacent region can be secured in the process of determining the reference image, a process of selecting an image of the adjacent region as the reference image is included, wherein a distance between a center of the selected adjacent region and the excluded region is the largest.

13. The operation method of a medical system according to claim 10, wherein when it is determined that the none of adjacent region can be secured in the process of determining the reference image, a process of selecting an image of a non-adjacent region from a plurality of non-adjacent regions being not adjacent to the reference position as the reference image is included, wherein a distance between a center of the selected non-adjacent region and the reference position is the smallest.

* * * * *